United States Patent [19]
Castelijns et al.

[11] Patent Number: 5,786,507
[45] Date of Patent: Jul. 28, 1998

[54] PROCESS FOR THE PREPARATION OF 3-PHENYLPROPIONIC ACID

[75] Inventors: Anna M. C. F. Castelijns, Beek; Johanna M. Hogeweg, Sittard; Simon P. J. M. van Nispen, Beek, all of Netherlands

[73] Assignee: DSM N.V., Heerlen, Netherlands

[21] Appl. No.: 834,380

[22] Filed: Apr. 16, 1997

Related U.S. Application Data

[63] Continuation of PCT/NL95/00358 Oct. 17, 1995.60]

[30] Foreign Application Priority Data

Oct. 17, 1994 [NL] Netherlands ............. 9401707

[51] Int. Cl.$^6$ ............. C07C 51/235; C07C 51/16
[52] U.S. Cl. ............. 562/412; 562/400; 562/405; 562/407; 562/409
[58] Field of Search ............. 562/400, 405, 562/407, 409, 412

[56] References Cited

U.S. PATENT DOCUMENTS 3,520,934 7/1970 Dunkel et al. ............. 260/599

FOREIGN PATENT DOCUMENTS 955421 4/1964 United Kingdom.

*Primary Examiner*—John Kight
*Assistant Examiner*—Howard C. Lee
*Attorney, Agent, or Firm*—Pillsbury, Madison & Sutro LLP, Cushman, Darby & Cushman IP Group

[57] ABSTRACT

Process for the preparation of 3-phenylpropionic acid in which 3-phenylpropanal is subjected to an oxidation, at elevated temperature, in particular at a temperature of between 40° and 80° C., using a medium containing molecular oxygen. A high degree of conversion and a high selectivity are obtained. The starting material 3-phenylpropanal can be prepared in a suitable manner through the hydrogenation of cinnamaldehyde in the presence of a Pd-containing catalyst, after which the reaction mixture obtained can without intermediate further processing be used in the oxidation reaction. The combination of the two process steps constitutes a simple, commercially attractive process for the preparation of 3-phenylpropionic acid using cinnamaldehyde as a starting material. 3-phenylpropionic acid can be used in particular in the preparation of pharmaceuticals such as HIV protease inhibitors.

12 Claims, No Drawings

5,786,507

PROCESS FOR THE PREPARATION OF 3-PHENYLPROPIONIC ACID

This is a continuation of International Appln. No. PCT/NL95/00358 filed Oct. 17, 1995 which designated the U.S.

FIELD OF THE INVENTION

Background Information

The invention relates to a process for the preparation of 3-phenylpropionic acid, in which 3-phenylpropanal is subjected to an oxidation, at elevated temperature, using a medium containing molecular oxygen.

A process is known from V. Haisman et al., Oxidation Communications 1983, 229. This publication describes the oxidation of 3-phenylpropanal with the aid of air, in heptane as a solvent, in the presence of cobalt acetate as a catalyst, at a temperature of 100° C. However, the selectivity towards 3-phenylpropionic acid was only 32%, 68% of the 3-phenylpropanal having been converted into benzoic acid. Such a process is hence commercially unattractive.

The invention now provides a process with which 3-phenylpropionic acid can be prepared with a high selectivity, in particular of over 85%, through the oxidation of 3-phenylpropanal, in a commercially very attractive process.

This is achieved according to the invention by carrying out the oxidation at a temperature between 40° and 80° C. It has been found that the selectivity of the reaction decreases at higher temperatures.

The applicant has surprisingly found that 3-phenylpropanal can be oxidized to 3-phenylpropionic acid, with a high yield and in a relatively short time, using a medium containing molecular oxygen, for example air. It has also been found that no catalyst need be used for this oxidation.

V. Miller and Rohde, Chem. Ber., 23, 1890, 1080, from 1890, already describes that, when exposed to air for some time, 3-phenylpropanal, like aldehydes in general, is converted into the corresponding acid. In particular it describes that 3-phenyl-2-methylpropanal is converted into 3-phenyl-2-methylpropionic acid when, poured out into a thin layer, it is exposed to air for several weeks. Such a process is however not applicable commercially.

In addition, many publications, including recent ones, are known that discuss the oxidation of aldehydes to the corresponding acids. EP-A-146373 (1985), for example, describes the oxidation of aldehydes in general, for example cinnamaldehyde, in a solvent, using hydrogen peroxide and chlorite as oxidation agents. EP-A-424242 (1991) describes the oxidation of 2-phenylpropanal in a solvent using hydrogen peroxide and a hydrogen halogenide. The oxidation agents used here are however less attractive from a practical point of view, because of the involved risk of salt formation and explosion hazard. Moreover, this process necessitates considerable dilution, which has an adverse effect on the production capacity.

SUMMARY AND OBJECTS OF THE INVENTION

The invention now provides a process with which 3-phenylpropionic acid can be prepared with a high selectivity, in particular of over 85%, through the oxidation of 3-phenylpropanal, in a commercially very attractive process.

This is achieved by carrying out the oxidation at a temperature between 40° and 80° C. It has been found that the selectivity of the reaction decreases at higher temperatures.

We have surprisingly found that 3-phenylpropanal can be oxidized to 3-phenylpropionic acid, with a high yield and in a relatively short time, using a medium containing molecular oxygen, for example air. It has also been found that no catalyst need be used for this oxidization.

DETAILED DESCRIPTION OF THE INVENTION

In the process according to the invention essentially pure 3-phenylpropanal is used as a starting product, which means that the starting product contains more than 60%, preferably more than 90%, 3-phenylpropanal. JACS, 72, 4939 (1950) describes an analytical method in which the oxidation of a mixture of 3-phenylpropanal and 2-phenylpropanal is mentioned in passing, without further technical details. However, the oxidation described in this publication results in only a low yield (approx. 55%).

With the process according to the invention it is possible to carry out the oxidation of phenylpropanal to phenylpropionic acid with a high degree of conversion and a high selectivity using a simple, cheap oxidation agent, for example air, without the necessity of using a solvent or a catalyst.

The pressure at which the oxidation is carried out is not critical and is usually between about atmospheric pressure and 5 MPa. Preferably the oxidation is carried out at elevated pressure, in particular of between 0.2 and 2 MPa. In practice it is often easier to retain a high oxygen concentration in the reaction mixture at elevated pressure. For good results in the oxidation it is of course important to ensure that the reaction mixture contains sufficient oxygen. The optimum conditions for the reaction hence for example consist of a suitable combination of the amount of oxygen supplied, the degree of mixing of the oxygen in the reaction mixture and the pressure at which the reaction takes place. A person skilled in the art will easily be able to determine the optimum combination for his situation.

The oxidation according to the invention is carried out at a temperature between 40° and 80° C. The highest selectivities were obtained at a temperature between 50° and 70° C., in particular between 55° and 65° C.

The oxidation can optionally be carried out in the presence of a solvent that is inert under the reaction conditions. Examples of suitable solvents are water, aliphatic or aromatic hydrocarbons, such as hexane, toluene or petroleum ether, or ethers, in particular methyl-t-butylether (MTBE). Preferably the oxidation is carried out without using a solvent, because then the production capacity is greatest and the further processing is simplest.

A suitable oxidation catalyst may optionally also be added. Preferably, however, the oxidation is carried out without a catalyst, because then a simpler process, without catalyst removal, is obtained.

The starting material 3-phenylpropanal can for example be obtained through hydrogenation of cinnamaldehyde. Preferably the hydrogenation is carried out with the aid of a Pd-containing catalyst, in the presence of a small amount of water, in particular 1–5 wt. %, relative to the amount of cinnamaldehyde.

This is because it has been found that cinnamaldehyde can be hydrogenated to 3-phenylpropanal with a high degree of conversion (>99%) and a high selectivity (>90%). The combined process, in which cinnamaldehyde is first hydrogenated to 3-phenylpropanal with the aid of $H_2$, in the presence of a Pd/C catalyst, after which the 3-phenylpropanal obtained is oxidized to 3-phenylpropionic acid using a medium containing molecular oxygen, constitutes a simple, cheap process for the preparation of 3-phenylpropionic acid, with which, to obtain a pure end product, it suffices to only purify the end product—for example through distillation or crystallisation; no intermediate further processing of the hydrogenation mixture is required.

The temperature at which the process according to the invention is carried out is not critical and is mostly around ambient temperature or elevated temperature, for example between 20° and 180° C. Preferably a temperature of between 55° and 90° C. is used because it seems that the highest selectivity can then be achieved. The pressure at which the process according to the invention is carried out is not critical either. Mostly atmospheric or elevated pressure is used, for example a pressure of between 0.1 and 15 MPa. Preferably the hydrogenation is carried out at a pressure of between 0.5 and 8 MPa, in particular of between 4 and 8 MPa.

Preferably Pd on a carrier is used as the Pd-containing catalyst, for example a Pd/C or a Pd/$Al_2O_3$ catalyst. The amount of catalyst to be used is not critical. Mostly use is made of between 0.01 and 2 wt. % Pd, preferably between 0.01 and 0.5 wt. % Pd, relative to the amount of cinnamaldehyde.

The selectivity of the hydrogenation can be further increased by adding an alkali salt of a weak acid to the reaction mixture. It has been found that potassium salt in particular increases the selectivity considerably. Acids with pKa values of 4 or higher are suitable for use as the weak acid, for example carbonic acid or carboxylic acids, in particular acetic acid, propanoic acid and butyric acid. The best results were obtained by adding potassium acetate.

The 3-phenylpropionic acid obtained can be used as an intermediate in the preparation of a number of end products for example pharmaceuticals, in particular, after conversion into the corresponding acid chloride, in the preparation of HIV protease inhibitors, known for example as L-735,524, as described in Tetrahedron Letters, Vol. 33, No. 3, 673–676, J. Med. Chem. 1992, 35, 1685–1701 and Chemistry & Engineering News, May 16, 1994, 6–7.

The invention will be further elucidated with reference to the following examples, without however being limited thereto.

EXAMPLE I

The oxidation was carried out in a reactor with a volume of 200 ml, which was fitted with baffles, a turbine stirrer and a gas inlet pipe so that the $N_2/O_2$ mixture was introduced directly below the stirrer, in order to ensure the best possible mixing of the gas and liquid. The reactor was also fitted with a condenser that was cooled to 0C. 127.7 g of crude phenylpropanal was introduced into the reactor, which had been obtained by hydrogenating pure cinnamaldehyde under the influence of a Pd/C catalyst and then removing the catalyst through filtration after the hydrogenation. This crude product had the following composition: 91.4 wt. % 3-phenylpropanal, 5.6 wt. % 3-phenylpropanol; 0.18 wt. % cinnamaldehyde, 0.27 wt. % cinnamic alcohol and 1.1 wt. % $H_2O$.

Then the dosage of air at a flow rate of 20 l/h was started, with simultaneous heating of the reaction mixture to 60° C. in 2 hours. The average percentage of $O_2$ in the off-gas was approximately 14%. Then the gas flow rate was increased to 30 l/h. After an overall reaction duration of 7.75 hours virtually no more oxygen was absorbed and the dosage of gas was stopped and the reaction mixture was cooled to room temperature. The reaction mixture now weighed approximately 136 g; GLC analysis showed that it had the following composition: 7.4 wt. % 3-phenylpropanal, 4.0 wt. % 3-phenylpropanol, 80.8 wt. % 3-phenylpropionic acid and 0.35 wt. % ethylbenzene. This corresponds to a degree of conversion of 3-phenylpropanal of approx. 91% and a selectivity towards 3-phenylpropionic acid of 91.5%.

EXAMPLE II

Now 121.8 g of crude phenylpropanal having the composition described for Example I was introduced into the same reactor as described for Example I.

The dosage of air at a flow rate of 20 l/h was then started, with stirring, with the simultaneous heating of the reaction mixture to 80° C. This temperature was reached after 15 minutes, after which the gas flow rate was increased to 30 l/h. The percentage of oxygen in the off-gas was 12–13% and gradually increased after 1 hour's reaction at 80° C. After approximately 7.5, hours' reaction at 80° C. virtually no more oxygen was absorbed and the dosage of gas was stopped and the reaction mixture was cooled to room temperature. The reaction mixture now weighed approximately 125.3 g; GLC analysis showed that it had the following composition: 4.3 wt. % 3-phenylpropanal, 2.6 wt. % 3-phenylpropanol; 78.8 wt. % 3-phenylpropionic acid and 0.4 wt. % ethylbenzene. This corresponds to a degree of conversion of 3-phenylpropanal of approximately 95% and a selectivity towards 3-phenylpropionic acid of 79.1%.

EXAMPLE III

The oxidation was carried out in a reactor with a volume of 200 liters, fitted with a stirrer, a gas inlet pipe and a condenser. A particular pressure could be set with the aid of a pressure control. 143.44 kg of 'crude phenylpropanal', obtained by hydrogenating pure cinnamaldehyde under the influence of Pd/C as a catalyst and by removing the catalyst through filtration afterwards, was introduced into this reactor. This crude product had the following composition: 93.0 wt. % 3-phenylpropanal, 2.6 wt. % 3-phenylpropanol and 0.9 wt. % $H_2O$.

Then the dosage of air at a flow rate of 73.2 $m^3$/h (15° C./1 bar) was started, with stirring, and the pressure in the reactor was set to 5 bar. The reaction mixture was then heated to 60° C. and kept at this temperature. The percentage of $O_2$ in the off-gas was originally 15–16% and gradually increased after 4 hours' reaction. After 7.4 hours' reaction virtually no more oxygen was absorbed and the gas flow was stopped and the mixture was cooled to room temperature. The reaction mixture now weighed 154.7 kg; GLC analysis showed that it had the following composition: 3.2 wt. % 3-phenylpropanal, 0.7 wt. % 3-phenylpropanol, 0.5 wt. % cinnamaldehyde; 85.1 wt. % 3-phenylpropionic acid; 0.74 wt. % ethylbenzene and 0.44 wt. % H20. This corresponds to a degree of conversion of 3-phenylpropanal of 96.3% and a selectivity towards 3-phenylpropionic acid of 91.6%.

What we claim is:

1. A process for the preparation of 3-phenylpropionic acid in which 3-phenylpropanal is subjected to an oxidation using a medium containing molecular oxygen, at an elevated temperature between 40° and 80° C.

2. The process according to claim 1, wherein the temperature is between 50° and 70° C.

3. The process according to claim 1 or claim 2, wherein the pressure is between 0.2 and 2 Mpa.

4. The process according to claim 1, wherein the oxidation is carried out in the absence of a solvent.

5. The process according to claim 1, wherein the oxidation is carried out in the absence of a catalyst.

6. The process according to claim 1, wherein the 3-phenylpropanal is first prepared by hydrogenating cinnamaldehyde using a Pd-containing catalyst.

7. The process according to claim 6, wherein the hydrogenation is carried out in the absence of a solvent.

8. The process according to claim 6, wherein the hydrogenation is carried out in the presence of 1–5 wt. % water.

9. The process according to claim 6, wherein the hydrogenation is carried out in the presence of potassium acetate.

10. The process according to claim 6, wherein the hydrogenation is carried out at a temperature of between 55° and 90° C.

11. The process according to claim 6, wherein the hydrogenation is carried out at a pressure of between 4 and 8 MPa.

12. A process for the preparation of 3-phenylpropionic acid which comprises the combination of steps of:

hydrogenating cinnamaldehyde using a Pd-containing catalyst, said hydrogenation being carried out in the presence of potassium acetate, and in the presence of 1-wt. % water, and said hydrogenation being carried out in the absence of a solvent, whereby 3-phenylpropanal is obtained;

subjecting said 3-phenylpropanal to oxidation using a medium containing molecular oxygen at an elevated temperature between 40° C. and 80° C., said oxidation being carried out in the absence of a solvent and in the absence of a catalyst.

* * * * *